United States Patent
Kubota et al.

[11] Patent Number: 6,087,520
[45] Date of Patent: Jul. 11, 2000

[54] PREPARATION OF 1,3-BIS(3-AMINOPROPYL) TETRAMETHYLDISILOXANE

[75] Inventors: Tohru Kubota; Mikio Endo, both of Nakakubiki-gun, Japan

[73] Assignee: Shin-Etsu Chemical Co., Ltd., Japan

[21] Appl. No.: 09/233,452

[22] Filed: Jan. 20, 1999

[30] Foreign Application Priority Data

Jan. 21, 1998 [JP] Japan .................................. 10-023940

[51] Int. Cl.$^7$ ................................ C07F 7/04; C07F 7/08
[52] U.S. Cl. .......................................... 556/425; 556/413
[58] Field of Search ..................... 556/413, 425

[56] References Cited

FOREIGN PATENT DOCUMENTS

| | | |
|---|---|---|
| 2304094 | 5/1989 | Japan . |
| 2-304094 | 12/1990 | Japan . |
| 7-55953 | 6/1995 | Japan . |
| 08134081 | 5/1996 | Japan . |

OTHER PUBLICATIONS

SAAM et al., "Preparation of 3–Triethoxysilylpropylamine and 1,3–Bis(3–aminopropyl)tetramethyl–disiloxane," *J. Org. Chem.*, vol. 24, pp. 119–120 (1959).

English Abstract of Japan Application No. 7–55953, Publication date, Dec. 17, 1990.

English Abstract of Japan Application No. 2–304094, Publication date, Jun. 14, 1995.

*Primary Examiner*—Johann Richter
*Assistant Examiner*—J. Parsa
*Attorney, Agent, or Firm*—Millen, White, Zelano & Branigan, P.C.

[57] ABSTRACT

By subjecting to hydrosilylation a hydrogendimethylalkoxysilane compound and an N-silylated allylamine compound in the presence of a platinum catalyst, adding an alcohol to the reaction product to effect desilylation reaction, and hydrolyzing the resulting 3-aminopropyldimethylalkoxysilane compound, 1,3-bis(3-aminopropyl)tetramethyldisiloxane is prepared. The end product free of isomers and of quality can be prepared through simple steps, at a low cost and in high yields.

18 Claims, No Drawings

PREPARATION OF 1,3-BIS(3-AMINOPROPYL) TETRAMETHYLDISILOXANE

This invention relates to a novel method for preparing 1,3-bis(3-aminopropyl)tetramethyldisiloxane which finds use as a modifier for polyimides for use as semiconductor insulating films and liquid crystal orientation films and as a modifier for polyamides and polyurethane.

BACKGROUND OF THE INVENTION

For the preparation of 1,3-bis(3-aminopropyl)-tetramethyldisiloxane, a method involving hydrosilylation reaction of an allylamine having an amino group protected with tetramethyldisiloxane, followed by deblocking of the protective group is known in the art. For example, use of trimethylsilylallylamine as the allylamine having an amino group protected is reported in J. Org. Chem, Vol. 24, page 119, 1959, and use of N-benzylideneallylamine is disclosed in JP-B 55953/1995.

These methods, however, have the problem that a substantial amount of an isomer in which internal addition has occurred rather than terminal addition forms during hydrosilylation reaction. As a result, 1-(2-aminopropyl)-3-(3-aminopropyl)tetramethyldisiloxane is admixed in the end compound. This isomer is less heat stable than the end compound, 1,3-bis(3-aminopropyl)tetramethyldisiloxane. When 1,3-bis(3-aminopropyl)tetramethyldisiloxane containing the isomer is used in the polyimide-modifying application where heat resistance is required, the performance is below the desired level.

Also, the step of deblocking the protective group from the reaction product resulting from hydrosilylation reaction tends to allow formation of by-products. In one example wherein the protective group is a trimethylsilyl group, equilibration reaction can occur when desilylation is carried out by adding water or alcohol, whereby (3-aminopropyl) pentamethyldisiloxane forms as a by-product, resulting in a reduced yield.

This problem can be avoided to some extent by a process including once deblocking the protective group with an acid, separating the resulting salt, and reacting with alkali. This process requires a very cumbersome operation.

Another known method for preparing 1,3-bis(3-aminopropyl)tetramethyldisiloxane is by subjecting an allylamine and a dimethylalkoxysilane to hydrosilylation reaction in the presence of a platinum complex catalyst having an olefin, a derivative thereof or a siloxane derivative thereof as the ligand and hydrolyzing the resulting product (see JP-A 304094/1990). Like the above method, this method also gives rise to the problem that a substantial amount of an isomer in which internal addition has occurred rather than terminal addition forms during hydrosilylation reaction, and as a result, 1-(2-aminopropyl)-3-(3-aminopropyl) tetramethyldisiloxane is admixed in the end compound. Moreover, since the catalyst used is special, it is not readily available and expensive.

There is a need to have a method for preparing 1,3-bis (3-aminopropyl)tetramethyldisiloxane of quality in a commercially advantageous manner.

SUMMARY OF THE INVENTION

An object of the invention is to provide a method for preparing 1,3-bis(3-aminopropyl)tetramethyldisiloxane of quality and free of isomers through simple steps and in high yields.

We have found that when a hydrogendimethylalkoxysilane compound of the following general formula (1) and an N-silylated allylamine compound of the following general formula (2) are subjected to hydrosilylation in the presence of a platinum catalyst, an alcohol is added to the reaction product to effect desilylation reaction, and the resulting 3-aminopropyldimethylalkoxysilane compound is hydrolyzed, quite unexpectedly, no isomer is formed during hydrosilylation reaction between the hydrogendimethylalkoxysilane compound and the trialkylsilyl-protected allylamine compound. Therefore, 1,3-bis(3-aminopropyl) tetramethyldisiloxane which is free of isomers and hence, of high purity and high performance is prepared through simple steps, at a low cost, and in high yields.

Accordingly, the invention provides a method for preparing 1,3-bis(3-aminopropyl)tetramethyldisiloxane. In a first step, a hydrogendimethylalkoxysilane compound of the following general formula (1):

$$HSi(CH_3)_2(OR^1) \tag{1}$$

wherein $R^1$ is a monovalent alkyl group and an N-silylated allylamine compound of the following general formula (2):

$$XYNCH_2CH=CH_2 \tag{2}$$

wherein X is a trialkylsilyl group and Y is hydrogen or a trimethylsilyl group are subjected to hydrosilylation in the presence of a platinum catalyst. In a second step, an alcohol is added to the reaction product of the first step to effect desilylation reaction. In a third step, the resulting 3-aminopropyldimethylalkoxysilane compound is hydrolyzed.

DETAILED DESCRIPTION OF THE INVENTION

In the method for producing 1,3-bis(3-aminopropyl)-tetramethyldisiloxane according to the present invention, one reactant used is a hydrogendimethylalkoxysilane compound represented by the following general formula (1):

$$HSi(CH_3)_2(OR^1) \tag{1}$$

wherein $R^1$ is a monovalent alkyl group.

In formula (1), the monovalent alkyl groups represented by $R^1$ may be either straight or cyclic and preferably have 1 to 6 carbon atoms. Exemplary are straight or branched alkyl groups such as methyl, ethyl, n-propyl, isopropyl, n-butyl, t-butyl, pentyl, and hexyl, and cyclic alkyl groups such as cyclohexyl.

Illustrative examples of the hydrogendimethylalkoxysilane compound of formula (1) include dimethylmethoxysilane, dimethylethoxysilane, dimethylpropoxysilane, dimethylisopropoxysilane, dimethylbutoxysilane, and dimethylcyclohexyloxysilane, with dimethylethoxysilane being preferred.

Another reactant used herein is an N-silylated allylamine compound of the following general formula (2):

$$XYNCH_2CH=CH_2 \tag{2}$$

wherein X is a trialkylsilyl group and Y is a hydrogen atom or trimethylsilyl group.

In formula (2), X represents trialkylsilyl groups, preferably trialkylsilyl groups whose alkyl has 1 to 6 carbon atoms, for example, trimethylsilyl, triethylsilyl, isopropyldimethylsilyl, t-butyldimethylsilyl, and cyclohexyldimethylsilyl. Y is hydrogen or a trimethylsilyl group.

Illustrative examples of the N-silylated allylamine compound of formula (2) include N-trimethylsilylallylamine, N-triethylsilylallylamine, N-isopropyldimethylsilylallylamine, N-t-butyldimethylsilylallylamine, N-cyclohexyldimethylsilylallylamine, N,N-bis (trimethylsilyl)allylamine, and N-triethylsilyl-N-trimethylsilylallylamine, with N,N-bis(trimethylsilyl) allylamine being especially preferred.

The hydrogendimethylalkoxysilane compound and the N-silylated allylamine compound are preferably used in such amounts that 0.5 to 3 mol, especially 1 to 1.5 mol of the hydrogendimethylalkoxysilane compound is available per mol of the N-silylated allylamine compound. If the amount of the hydrogendimethylalkoxysilane compound is less than 0.5 mol, the N-silylated allylamine compound would become excessive and left after the reaction. Inversely, if the amount of the hydrogendimethylalkoxysilane compound is more than 3 mol, it would become excessive and left after the reaction.

For hydrosilylation reaction, the reactants may be added in any desired way, for example, of adding the N-silylated allylamine compound to the hydrogendimethylalkoxysilane compound, or inversely, adding the hydrogendimethylalkoxysilane compound to the N-silylated allylamine compound.

The platinum catalyst used for hydrosilylation reaction may be selected from among platinum metal, platinum compounds such as chloroplatinic acid, $[PtCl_2(PPh_3)_2]$, and platinum complexes having olefins or siloxane derivatives thereof as the ligand. From the standpoints of availability and cost, chloroplatinic acid or an alcohol solution thereof is preferred. The amount of the platinum catalyst may be determined as appropriate although an appropriate amount is about 0.1 to 1,000 parts, especially about 10 to 200 parts by weight of platinum metal per million parts by weight of the substrate, N-silylated allylamine compound.

For hydrosilylation, a reaction temperature of 0 to 200° C., especially 50 to 120° C. is appropriate.

According to the invention, the hydrosilylation reaction is followed by desilylation reaction which is effected by adding an alcohol to the reaction product. The alcohol used for desilylation reaction may be any of alcohols inclusive of polyhydric alcohols although monohydric alcohols such as methanol and ethanol are preferable from the standpoints of cost and ease of handling.

An appropriate amount of alcohol used is at least one equivalent, especially 1 to 5 equivalents relative to the silyl group in the N-silylated allylamine compound of formula (2) used in the hydrosilylation reaction.

For the desilylation reaction with alcohol, no catalyst is necessary although salts such as ammonium salts and acids such as hydrogen chloride, p-toluenesulfonic acid, and dodecylbenzenesulfonic acid may be added as the catalyst for reducing the reaction time. These catalysts are used in conventional amounts.

For desilylation, a reaction temperature of 0 to 200° C. is appropriate.

In the last step of the inventive method, the 3-aminopropyldimethylalkoxysilane compound resulting from the foregoing hydrosilylation and desilylation is hydrolyzed, thereby obtaining the end product, 1,3-bis(3-aminopropyl)-tetramethyldisiloxane.

Hydrolysis of 3-aminopropyldimethylalkoxysilane can be effected by adding water directly to the reaction solution at the end of desilylation reaction. Preferably, the residual alcohol and trialkylalkoxysilane by-products are removed by distillation or other suitable means from the reaction solution resulting from desilylation reaction before water is added to effect hydrolysis. If trialkylalkoxysilane by-products resulting from desilylation reaction co-exist during hydrolysis, disiloxane compounds with these by-products can form, reducing the percent yield of the end product.

In the method of the invention, hydrosilylation, desilylation, and hydrolysis can be carried out in an essentially solventless system. If desired, aprotic solvents such as toluene, xylene, hexane, decane, and tetrahydrofuran are used.

At the end of hydrolysis, the end product, 1,3-bis(3-aminopropyl)tetramethyldisiloxane can be recovered by conventional means, typically vacuum distillation.

There has been described a method for preparing 1,3-bis (3-aminopropyl)tetramethyldisiloxane through hydrosilylation, desilylation, and hydrolysis. The end product free of isomers and of quality can be prepared through simple steps, at a low cost and in high yields. The 1,3-bis (3-aminopropyl)tetramethyldisiloxane obtained by the inventive method exhibits high performance including heat resistance and thus finds advantageous use as a modifier for polyimides for use as semiconductor insulating films and liquid crystal orientation films and as a modifier for polyamides and polyurethane.

EXAMPLE

Examples of the invention are given below by way of illustration and not by way of limitation.

Example 1

A 1-liter glass flask equipped with a stirrer, reflux condenser, thermometer and dropping funnel was charged with 201.5 g (1.0 mol) of N,N-bis(trimethylsilyl)allylamine and 0.98 g of a 4% isopropyl alcohol solution of $H_2PtCl_6 \cdot 6H_2O$. From the funnel, 104.2 g (1.0 mol) of dimethylethoxysilane was added dropwise to the flask at 70° C. over 3 hour for hydrosilylation reaction, and the reaction solution was ripened for one hour at the temperature. After 368.5 g of ethanol and 1.7 g of dodecylbenzenesulfonic acid were added, the reaction solution was refluxed for 6 hours, completing desilylation reaction.

The reaction solution was transferred to a distillation apparatus where the ethanol and trimethylethoxysilane were distilled off under atmospheric pressure. Water, 10 g, was added to the remainder, which was refluxed for 2 hours. Vacuum distillation was then carried out to collect a fraction of 99 to 101° C./2 mmHg, obtaining 106.9 g (yield 86%) of 1,3-bis(3-aminopropyl)tetramethyldisiloxane. The compound obtained was analyzed by gas chromatography to find that it was free of 1-(2-aminopropyl)-3-(3-aminopropyl)-tetramethyldisiloxane.

Example 2

Hydrosilylation and desilylation reactions were carried out as in Example 1 except that 368.5 g of ethanol used in the desilylation reaction was replaced by 256.3 g of methanol.

The reaction solution was transferred to a distillation apparatus where the methanol, trimethylmethoxysilane and trimethylethoxysilane were distilled off under atmospheric pressure. Water, 10 g, was added to the remainder, which was refluxed for 2 hours. Vacuum distillation was then carried out to collect a fraction of 85 to 87° C./1 mmHg, obtaining 104.2 g (yield 84%) of 1,3-bis(3-aminopropyl)-tetramethyldisiloxane. The compound obtained was analyzed by gas chromatography to find that it was free of 1-(2-aminopropyl)-3-(3-aminopropyl)tetramethyldisiloxane.

Example 3

A 1-liter glass flask equipped with a stirrer, reflux condenser, thermometer and dropping funnel was charged with 129.3 g (1.0 mol) of N-trimethylsilylallylamine and 0.98 g of a 4% isopropyl alcohol solution of $H_2PtCl_6.6H_2O$. From the funnel, 104.2 g (1.0 mol) of dimethylethoxysilane was added dropwise to the flask at 70° C. over 3 hours for hydrosilylation reaction, and the reaction solution was ripened for one hour at the temperature. After 50.7 g of ethanol was added, the reaction solution was stirred at 50° C. for one hour, completing desilylation reaction.

The reaction solution was transferred to a distillation apparatus where the ethanol and trimethylethoxysilane were distilled off under atmospheric pressure. Water, 10 g, was added to the remainder, which was refluxed for 2 hours. Vacuum distillation was then carried out to collect a fraction of 99 to 101° C./2 mmHg, obtaining 99.8 g (yield 80%) of 3-bis(3-aminopropyl)tetramethyldisiloxane. The compound obtained was analyzed by gas chromatography to find that it was free of 1-(2-aminopropyl)-3-(3-aminopropyl)tetramethyldisiloxane.

Example 4

Hydrosilylation and desilylation reactions were carried out as in Example 3 except that 129.3 g (1.0 mol) of N-trimethylsilylallylamine was replaced by 171.4 g (1.0 mol) of N-triethylsilylallylamine.

The reaction solution was transferred to a distillation apparatus where the ethanol and triethylethoxysilane were distilled off under atmospheric pressure. Water, 10 g, was added to the remainder, which was refluxed for 2 hours. Vacuum distillation was then carried out to collect a fraction of 91 to 93° C./1.5 mmHg, obtaining 88.4 g (yield 71%) of 1,3-bis(3-aminopropyl)tetramethyldisiloxane. The compound obtained was analyzed by gas chromatography to find that it was free of 1-(2-aminopropyl)-3-(3-aminopropyl)-tetramethyldisiloxane.

Comparative Example 1

A 1-liter glass flask equipped with a stirrer, reflux condenser, thermometer and dropping funnel was charged with 129.3 g (1.0 mol) of N-trimethylsilylallylamine and 0.98 g of a 4% isopropyl alcohol solution of $H_2PtCl_6.6H_2O$. From the funnel, 67.2 g (0.5 mol) of 1,1,3,3-tetramethyldisiloxane was added dropwise to the flask at 70° C. over 3 hours for hydrosilylation reaction, and the reaction solution was ripened for one hour at the temperature. After 64.0 g of methanol was added, the reaction solution was refluxed for one hour for desilylation reaction. The reaction completed, but large amounts of by-products, 3-aminopropylpentamethyldisiloxane and 3-aminopropyldimethylmethoxysilane formed in the reaction solution. The reaction solution was analyzed by gas chromatography to find that it contained 7% of 1-(2-aminopropyl)-3-(3-aminopropyl)tetramethyldisiloxane based on the weight of the end compound, 1,3-bis(3-aminopropyl)-tetramethyldisiloxane.

Comparative Example 2

A 500-ml glass flask equipped with a stirrer, reflux condenser, thermometer and dropping funnel was charged with 67.29 g (0.5 mol) of 1,1,3,3-tetramethyldisiloxane, 150 g of xylene and 0.15 g of a 4% isopropyl alcohol solution of $H_2PtCl_6.6H_2O$, and heated at 100° C. From the funnel, 145.2 g (1.0 mol) of N-benzylideneallylamine was added dropwise to the flask over 2 hours for hydrosilylation reaction. After the completion of addition, the reaction solution was ripened at 150° C. for 3 hours. Thereafter, 275 g of 17% hydrochloric acid was added to the reaction solution to effect hydrolysis for deblocking. The water layer was separated and washed with an equal amount of toluene. By adding 47.5 g of sodium hydroxide and 140 g of water, 1,3-bis(3-aminopropyl)tetramethyldisiloxane was liberated. The compound obtained was analyzed by gas chromatography to find that it contained 13% of 1-(2-aminopropyl)-3-(3-aminopropyl)-tetramethyldisiloxane based on the weight of the end compound, 1,3-bis(3-aminopropyl)tetramethyldisiloxane.

Japanese Patent Application No. 023940/1998 is incorporated herein by reference.

The invention has been described in detail with particular reference to preferred embodiments thereof, but it will be understood that variations and modifications can be effected within the spirit and scope of the invention.

What is claimed is:

1. A method for preparing 1,3-bis(3-aminopropyl)-tetramethyldisiloxane, comprising the steps of:

subjecting to hydrosilylation a hydrogendimethylalkoxysilane compound of the following general formula (1):

$$HSi(CH_3)_2(OR^1) \qquad (1)$$

wherein $R^1$ is a monovalent alkyl group and an N-silylated allylamine compound of the following general formula (2):

$$XYNCH_2CH=CH_2 \qquad (2)$$

wherein X is a trialkylsilyl group and Y is hydrogen or a trimethylsilyl group, in the presence of a platinum catalyst, adding an alcohol to the reaction product to effect desilylation reaction, and hydrolyzing the resulting 3-aminopropyldimethylalkoxysilane compound.

2. The method of claim 1 wherein the N-silylated allylamine compound of formula (2) is N,N-bis(trimethylsilyl)allylamine.

3. A method as claimed in claim 1, wherein the hydrogendimethylalkoxysilane compound is present in an amount of from 0.5 to 3 mol per mol of the N-silyated allylamine.

4. A method as claimed in claim 1, wherein the hydrogendimethylalkoxysilane compound is present in an amount of from 1.0 to 1.5 mol per mol of the N-silyated allylamine.

5. A method as claimed in claim 1, wherein the platinum catalyst is selected from the group consisting of platinum metal, platinum compounds, and platinum complexes having olefins or siloxane derivatives as the ligand.

6. A method as claimed in claim 1, wherein the platinum catalyst is chloroplatinic acid.

7. A method as claimed in claim 6, wherein the platinum catalyst is chloroplatinic acid in an alcohol solution.

8. A method as claimed in claim 1, wherein the hydrosilylation is carried out at a temperature of from 0 to 200 degrees C.

9. A method as claimed in claim 8, wherein the hydrosilylation is carried out at a temperature of from 50 to 120 degrees C.

10. A method as claimed in claim 1, wherein the alcohol is added in an amount of from 1 to 5 equivalents relative to the silyl group in the N-silylated allylamine compound of formula 2.

11. A method as claimed in claim 1, wherein the desilylation is carried out at a temperature of from 0 to 200 degrees C.

12. A method as claimed in claim 1, further comprising, before hydrolysis, removing the alcohol and any trialkoxysilane by-products by distillation.

13. A method as claimed in claim 1, further comprising the step of vacuum distillation of the 3-aminopropyldimethylalkoxysilane compound.

14. A method for preparing 1,3-bis(3-aminopropyl)-tetramethyidisiloxane, comprising the steps of:

subjecting to hydrosilylation at from 0 to 200 degrees C a hydrogendimethylalkoxysilane compound of the following general formula (1):

$$HSi(CH_3)_2(OR^1) \quad (1)$$

wherein $R^1$ is a monovalent alkyl group and 1 mol (per 0.5 to 3 mols of the hydrogendimethylalkoxysilane compound) of an N-silylated allylamine compound of the following general formula (2):

$$XYNCH_2CH=CH_2 \quad (2)$$

wherein X is a trialkylsilyl group and Y is hydrogen or a trimethylsilyl group, in the presence of chloroplatinic acid, adding 1 to 5 equivalents, relative to the silyl group in the N-silyated allylamine compound of formula 2, an alcohol to the reaction product to effect desilylation reaction, and hydrolyzing the resulting 3-aminopropyldimethylalkoxysilane compound.

15. A method as claimed in claim 14, wherein the desilylation is carried out at a temperature of from 0 to 200 degrees C.

16. A method as claimed in claim 14, further comprising the step of vacuum distillation of the 3-aminopropyldimethylalkoxysilane compound.

17. A method as claimed in claim 1, wherein the 3-aminopropyldimethylalkoxysilane formed is essentially isomer-free.

18. A method as claimed in claim 14, wherein the 3-aminopropyldimethylalkoxysilane formed is essentially isomer-free.

* * * * *